US008758509B2

(12) United States Patent
Twitchen et al.

(10) Patent No.: US 8,758,509 B2

(45) Date of Patent: Jun. 24, 2014

(54) DIAMOND SENSORS, DETECTORS, AND QUANTUM DEVICES

(75) Inventors: Daniel James Twitchen, Santa Clara, CA (US); Matthew Lee Markham, Oxfordshire (GB)

(73) Assignee: Element Six Limited, Ballasalla (IM)

(*) Notice: Subject to any disclaimer, the term of this patent is extended or adjusted under 35 U.S.C. 154(b) by 0 days.

(21) Appl. No.: 14/115,815

(22) PCT Filed: May 10, 2012

(86) PCT No.: PCT/EP2012/058682

§ 371 (c)(1), (2), (4) Date: Nov. 13, 2013

(87) PCT Pub. No.: WO2012/159896

PCT Pub. Date: Nov. 29, 2012

(65) Prior Publication Data

US 2014/0077231 A1 Mar. 20, 2014

Related U.S. Application Data

(60) Provisional application No. 61/489,601, filed on May 24, 2011.

(30) Foreign Application Priority Data

May 24, 2011 (GB) .................................. 1108644.4

(51) Int. Cl.
*C30B 29/04* (2006.01)

(52) U.S. Cl.
USPC .............. 117/86; 117/104; 117/929; 423/446

(58) Field of Classification Search
USPC ............................ 117/86, 104, 929; 423/446
See application file for complete search history.

(56) References Cited

U.S. PATENT DOCUMENTS

| | | | |
|---|---|---|---|
| 6,582,513 | B1 | 6/2003 | Linares et al. |
| 2005/0181210 | A1 | 8/2005 | Doering et al. |
| 2006/0234419 | A1 | 10/2006 | Linares et al. |
| 2011/0062957 | A1 | 3/2011 | Fu et al. |

FOREIGN PATENT DOCUMENTS

| | | | |
|---|---|---|---|
| WO | 2007/009037 | A1 | 1/2007 |
| WO | 2010/010344 | A1 | 1/2010 |
| WO | 2010/010352 | A1 | 1/2010 |

OTHER PUBLICATIONS

Search Report for GB1208201.2 dated Oct. 12, 2012.
Search Report for GB1108644.4 dated Sep. 21, 2011.
International Search Report for PCT/EP2012/058682 dated Aug. 9, 2012.
Steinert et al., "High sensitivity magnetic imaging using an array of spins in diamond", Review of Scientific Instruments 81, 043705 (2010).

(Continued)

*Primary Examiner* — Bob M Kunemund

(74) *Attorney, Agent, or Firm* — Bryan Cave LLP

(57) ABSTRACT

A thin plate of synthetic single crystal diamond material, the thin plate of synthetic single crystal diamond material having: a thickness in a range 100 nm to 50 μιη; a concentration of quantum spin defects greater than 0.1 ppb (parts-per-billion); a concentration of point defects other than the quantum spin defects of below 200 ppm (parts-per-million); and wherein at least one major face of the thin plate of synthetic single crystal diamond material comprises surface termination species which have zero nuclear spin and/or zero electron spin.

15 Claims, 10 Drawing Sheets

N
V
C

(56) References Cited

OTHER PUBLICATIONS

Kennedy et al., "Single-Qubit Operations with the Nitrogen-Vacancy Center in Diamond," Phys. Stat. Sol. (b) 233, No. 3, 416-426 (2002).
Kennedy et al., "Long coherence times at 300 K for nitrogen-vacancy center spins in diamond grown by chemical vapor deposition," Appl. Phys. Lett. vol. 83, No. 20, 4190-4192 (2003).
Olivero et al., "Ion-Beam-Assisted Lift-Off Technique for Three-Dimensional Micromachining of Freestanding Single-Crystal Diamond," Advanced Materials, vol. 17, No. 20, 2005, 2427-2430.
Markham et al., "CVD diamond for spintronics," Diamond and Related Materials, vol. 20, No. 2, 2010, 134-139.
Orwa et al., "Engineering of nitrogen-vacancy color centers in high purity diamond by ion implantation and annealing," Journal of Applied Physics, vol. 109, No. 8, 2011, 83530-83530.

DIAMOND SENSORS, DETECTORS, AND QUANTUM DEVICES

FIELD OF INVENTION

The present invention relates to synthetic diamond material for use in sensing, detecting and quantum processing applications.

BACKGROUND OF INVENTION

Point defects in synthetic diamond material, particularly quantum spin defects and/or optically active defects, have been proposed for use in various sensing, detecting, and quantum processing applications including: magnetometers; spin resonance devices such as nuclear magnetic resonance (NMR) and electron spin resonance (ESR) devices; spin resonance imaging devices for magnetic resonance imaging (MRI); and quantum information processing devices such as for quantum computing.

Many point defects have been studied in synthetic diamond material including: silicon containing defects such as silicon-vacancy defects (Si-V), silicon di-vacancy defects (Si-$V_2$), silicon-vacancy-hydrogen defects (Si-V:H), silicon di-vacancy hydrogen defects (S-$V_2$:H); nickel containing defect; chromium containing defects; and nitrogen containing defects such as nitrogen-vacancy defects (N-V), di-nitrogen vacancy defects (N-V-N), and nitrogen-vacancy-hydrogen defects (N-V-H). These defects are typically found in a neutral charge state or in a negative charge state. It will be noted that these point defects extend over more than one crystal lattice point. The term point defect as used herein is intended to encompass such defects but not include larger cluster defects, such as those extending over ten or more lattice points, or extended defects such as dislocations which may extend over many lattice points.

It has been found that certain defects in synthetic diamond material are particularly useful for sensing, detecting, and quantum processing applications. For example, the negatively charged nitrogen-vacancy defect ($NV^-$) in synthetic diamond material has attracted a lot of interest as a useful quantum spin defect because it has several desirable features including:

(i) Its electron spin states can be coherently manipulated with high fidelity owing to an extremely long coherence time (which may be quantified and compared using the transverse relaxation time $T_2$);

(ii) Its electronic structure allows the defect to be optically pumped into its electronic ground state allowing such defects to be placed into a specific electronic spin state even at non-cryogenic temperatures. This can negate the requirement for expensive and bulky cryogenic cooling apparatus for certain applications where miniaturization is desired. Furthermore, the defect can function as a source of photons which all have the same spin state; and (iii) Its electronic structure comprises emissive and non-emissive electron spin states which allows the electron spin state of the defect to be read out through photons. This is convenient for reading out information from synthetic diamond material used in sensing applications such as magnetometry, spin resonance spectroscopy and imaging. Furthermore, it is a key ingredient towards using the $NV^-$ defects as qubits for long-distance quantum communications and scalable quantum computation. Such results make the $NV^-$ defect a competitive candidate for solid-state quantum information processing (QIP).

The $NV^-$ defect in diamond consists of a substitutional nitrogen atom adjacent to a carbon vacancy as shown in FIG. 1*a*. Its two unpaired electrons form a spin triplet in the electronic ground state ($^3$A), the degenerate $m_s=\pm1$ sublevels being separated from the $m_s=0$ level by 2.87 GHz. The electronic structure of the $NV^-$ defect is illustrated in FIG. 1b from Steingert et al. "High sensitivity magnetic imaging using an array of spins in diamond", Review of Scientific Instruments 81, 043705 (2010). The $m_s=0$ sublevel exhibits a high fluorescence rate when optically pumped, for example using a 532 nm laser. In contrast, when the defect is excited in the $m_s=\pm1$ levels, it exhibits a higher probability to cross over to the non-radiative singlet state ($^1$A) followed by a subsequent relaxation into $m_s=0$. As a result, the spin state can be optically read out, the $m_s=0$ state being "bright" and the $m_s=\pm1$ states being dark. When an external magnetic field is applied, the degeneracy of the spin sublevels $m_s=\pm1$ is broken via Zeeman splitting. This causes the resonance lines to split depending on the applied magnetic field magnitude and its direction. This dependency can be used for vector magnetometry as the resonant spin transitions can be probed by sweeping the microwave (MW) frequency resulting in characteristic dips in the optically detected magnetic resonance (ODMR) spectrum as shown in FIG. 2a from Steinert et al.

Steinert et al. employed ion implantation to create a homogenous layer of negatively charged $NV^-$ centres into an ultrapure {100} type IIa diamond. The ensemble $NV^-$ sensor was found to offer a higher magnetic sensitivity due to the amplified fluorescence signal from a plurality of sensing spins. Another option is vector reconstruction since the diamond lattice imposes four distinct tetrahedral $NV^-$ orientations as shown in FIG. 2b from Steinert et al. The magnetic field projections along each of these axes can be measured as a single composite spectrum and a numerical algorithm used to reconstruct the full magnetic field vector. The magnitude (B) and orientation ($\theta_B$, $\phi_B$) of the external magnetic field can be calculated by analyzing the ODMR spectra based on an unconstrained least-square algorithm.

One major problem in producing materials suitable for quantum applications is preventing quantum spin defects from decohering, or at least lengthening the time a system takes to decohere (i.e. lengthening the "decoherence time"). A long $T_2$ time is desirable in applications such as quantum computing as it allows more time for the operation of an array of quantum gates and thus allows more complex quantum computations to be performed. A long $T_2$ time is also desirable for increasing sensitivity to changes in the electric and magnetic environment in sensing applications.

Kennedy et al. have disclosed that the decoherence time of $NV^-$ defects in synthetic CVD (chemical vapour deposited) diamond material is longer than for $NV^-$ defects in synthetic HPHT (high pressure high temperature) diamond material and that low nitrogen concentration in synthetic CVD diamond material is a factor in achieving longer decoherence times (see, for example, Phys. Stat. Sol. (b) 233, no. 3, 416-426 (2002) and Appl. Phys. Lett. vol. 83, no. 20, 4190-4192 (2003)). Kennedy et al. disclose an $NV^-$ defect decoherence time of 58 μs at room temperature (300 K) for a CVD diamond material having a single substitutional nitrogen concentration of 30 ppb.

Subsequently, through careful use and control of various manufacturing techniques Scarsbrook et al. have fabricated a single crystal CVD diamond material with $NV^-$ defects having a decoherence time greater than 600 μs (see, for example, WO 2010010344 and WO 2010010352).

WO 2010010344 discloses that single crystal synthetic CVD diamond material which has a high chemical purity, i.e.

a low nitrogen content, and wherein a surface of the diamond material has been processed to minimise the presence of crystal defects, can be used to form a solid state system comprising a quantum spin defect. Where such materials are used as a host for quantum spin defects, long $T_2$ times are obtained at room temperature and the frequency of the optical transitions used to read/write to devices are stable.

WO 2010010352 discloses that by carefully controlling the conditions under which single crystal synthetic CVD diamond material is prepared, it is possible to provide synthetic diamond material which combines a very high chemical purity, a very high crystallographic purity, and a very high isotopic purity. By controlling the chemical purity, crystallographic purity, and isotopic purity of the material used in the CVD process, it is possible to obtain synthetic diamond material which is particularly suitable for use as a host for a quantum spin defect. Where such materials are used as a host for quantum spin defects, long $T_2$ times are obtained at room temperature and the frequency of the optical transitions used to read/write to the devices are stable. A layer of synthetic CVD diamond material is disclosed which has a low nitrogen concentration and a low concentration of $^{13}C$. The layer of synthetic diamond material has very low impurity levels and very low associated point defect levels. In addition, the layer of synthetic CVD diamond material has a low dislocation density, low strain, and vacancy and self-interstitial concentrations which are sufficiently close to thermodynamic values associated with the growth temperature that its optical absorption is essentially that of a perfect diamond lattice.

In light of the above, it is evident that WO 2010010344 and WO 2010010352 disclose methods of manufacturing very high quality "quantum grade" single crystal synthetic CVD diamond material. The term "quantum grade" is used herein for diamond material which is suitable for use in applications that utilize the material's quantum spin properties. Specifically, the quantum grade diamond material's high purity makes it possible to isolate single defect centres using optical techniques known to the person skilled in the art. The term "quantum diamond material" is also used to refer to such material.

One problem with quantum materials is that single photon emission from quantum spin defects in such materials can be very weak. For example, $NV^-$ defects in diamond exhibit a broad spectral emission associated with a Debye-Waller factor of the order of 0.05, even at low temperature. Emission of single photons in the Zero-Phonon Line (ZPL) is then extremely weak, typically of the order of a few thousands of photons per second. Such counting rates might be insufficient for the realization of advanced QIP protocols based on coupling between spin states and optical transitions within reasonable data acquisition times.

The problem of weak emission may be alleviated to some extent by increasing the number of quantum spin defects such that a large number of emitting species exists in the material. For example, the number of $NV^-$ defects may be increased by increasing the concentration of nitrogen in the diamond material. Synthetic CVD diamond material can be grown with >10 ppm nitrogen. However, the presence of nitrogen at high concentrations in the CVD growth process typically results in the incorporation of other defects which: (i) leads to an increase in diamond absorption affecting the efficiency of excitation of $NV^-$ defects and light collection therefrom; and (ii) leads to a reduction in the decoherence time due to decoherence mechanisms linked to other defects. While these other defects can be reduced by application of appropriate high temperature annealing techniques, in some applications this is undesirable due to residual graphitization and other potential complications.

In light of the above, while the longest decoherence times are reported for very low defect synthetic CVD diamond materials, the sensitivity these synthetic CVD diamond materials offer are compromised by the reduced $NV^-$ defect concentration. Furthermore, methods to increase the $NV^-$ defect concentration through implantation have limited value due to residual spin defects introduced due to implantation damage.

It is an aim of certain embodiments of the present invention to at least partially solve one or more of the aforementioned problems.

In relation to the above, US2006/0234419 and U.S. Pat. No. 6,582,513 disclose that CVD diamond can be grown with layers of controlled purity and thickness. It is further disclosed that since the number of atoms of nitrogen in a diamond film will be a function of concentration and thickness, $NV^-$ defects may be isolated from other defects. In other words, given a known concentration of NV defects that will be formed in a given volume of CVD grown diamond, making the diamond layer very thin assures that very few NV defects are formed, and are thus isolated from each other. WO2007/009037 also discloses that the isolation of NV defects is a function of thickness and nitrogen content and that a thin layer of CVD diamond material can provide isolated NV defects. Implantation and release is disclosed as a means for separating a thin as-grown layer of CVD diamond material from a substrate on which it is grown. Such an implantation and release mechanism for separating thin films of as-grown CVD diamond material from a substrate is also disclosed in US2005/0181210.

SUMMARY OF INVENTION

The present inventors have realized that it is problematic to introduce a high concentration of quantum spin defects into synthetic CVD diamond material without detrimentally affecting the optical properties of the material and the decoherence time of the quantum spin defects. Furthermore, the present inventors have realized that bulk samples of synthetic HPHT diamond material have a concentration of quantum spin defects, such as $NV^-$ defects, which is too high to optically isolate individual defects and that the high number of quantum spin defects leads to a reduction in decoherence time. The present inventors have found that if a synthetic diamond material having a relatively high concentration of quantum spin defects is processed to form a very thin layer of such material, it is possible for individual quantum spin defects to be optically isolated. Furthermore, by processing the material to be very thin then optical absorption within the synthetic diamond material is reduced thus increasing the efficiency of excitation of the quantum spin defects and light collection therefrom. In this way, synthetic diamond material which was not previously suitable for quantum spin applications may be processed into a form which is suitable for such applications. For example, the nitrogen concentration and film thickness of synthetic diamond material can be balanced so that quantum spin defects are optically isolated and have good optical efficiency in terms of excitation and light collection. This may be particularly useful for synthetic HPHT diamond material where thicker layers of material have a defect concentration which is too high to optically isolate individual quantum spin defects.

In some respects this balancing of quantum spin defect concentration and film thickness is similar to that described in prior art documents such as US2006/0234419 and WO2007/

009037. However, it has been found that while balancing quantum spin defect concentration and film thickness in this manner can result in optically isolated quantum spin defects, the decoherence time $T_2$ of the isolated quantum spin defects is still too low for many sensing and quantum processing applications.

One way to increase the decoherence time of quantum spin defects is to ensure that the concentration of other point defects within the synthetic diamond material is low so as to avoid dipole coupling and/or strain resulting in a decrease in decoherence time of the quantum spin defects. However, for thin plates of material it has been found that this is still insufficient to achieve very high decoherence times.

Reducing the concentration of the quantum spin defects themselves can increase decoherence times of individual quantum spin defects. However, while this will increase the sensitivity of each individual quantum spin defect, a reduction in the number of quantum spin defects will reduce the overall sensitivity of the material. What is considered important for many quantum sensing applications is the product of the quantum spin defect concentration and the decoherence time $T_2$ of the quantum spin defects. Preferably this product should be at least 0.1 ppm μs, 1 ppm μs, 10 ppm μs, 20 ppm μs, 30 ppm μs, 50 ppm μs, 100 ppm μs, 200 ppm μs, 500 ppm μs, 1000 ppm μs, or 5000 ppm μs. The maximum for this product is considered to be less than 10000 ppm μs.

While improved values for the product of the quantum spin defect concentration and the decoherence time $T_2$ of the quantum spin defects can be achieved by controlling the concentration of quantum spin defects and the concentration of other point defects as previously described, for thin plates of material it has also been found that surface termination groups can adversely interact with nearby quantum spin defects thus reducing the value of the product by reducing $T_2$. This is particularly problematic for thin plates of diamond material which have a large surface area to volume ratio with a large number of quantum spin defects located relatively close to the surface of the material. As such, in order to increase the product of the quantum spin defect concentration and the decoherence time $T_2$ of the quantum spin defects it is also considered necessary to control the surface termination of the thin plate of diamond material. In particular, it is considered advantageous to treat the plate of diamond material to provide surface termination species which have zero nuclear spin or zero electron spin, preferably both zero nuclear spin and zero electron spin. An example of such a species is $^{16}O$.

In light of the above, the present inventors consider that to achieve plates of diamond material with high quantum sensing capability requires the combination of four different parameters: (i) controlled plate thickness; (ii) controlled quantum spin defect concentration; (iii) controlled concentration of other point defects; and (iv) controlled surface termination.

Accordingly, a first aspect of the present invention provides a thin plate of synthetic single crystal diamond material, the thin plate of synthetic single crystal diamond material having:

- a thickness in a range 100 nm to 50 μm;
- a concentration of quantum spin defects greater than 0.1 ppb (parts-per-billion);
- a concentration of point defects other than the quantum spin defects of below 200 ppm (parts-per-million); and
- wherein at least one major face of the thin plate of synthetic single crystal diamond material comprises surface termination species which have zero nuclear spin and/or zero electron spin.

According to a second aspect of the present invention there is provided a method of manufacturing a thin plate of synthetic single crystal diamond material comprising:

- providing a synthetic single crystal diamond material having a concentration of quantum spin defects greater than 0.1 ppb (parts-per-billion) and a concentration of point defects other than the quantum spin defects of below 200 ppm (parts-per-million);
- processing the synthetic single crystal diamond material to form a thin plate having a thickness in a range 100 nm to 50 μm; and
- treating the thin plate of synthetic single crystal diamond material such that at least one major face of the thin plate of synthetic single crystal diamond material comprises surface termination species which have zero nuclear spin and/or zero electron spin.

According to a third aspect of the present invention there is provided a synthetic diamond device component for use in a sensing, detecting or quantum spin device, said device component comprising a thin plate of synthetic single crystal diamond material as described above.

According to a fourth aspect of the present invention there is provided a device comprising a device component as described above. The device may comprise a light source for optically pumping one or more of the plurality of quantum spin defects in the thin plate of single crystal synthetic diamond material.

BRIEF DESCRIPTION OF THE DRAWINGS

For a better understanding of the present invention and to show how the same may be carried into effect, embodiments of the present invention will now be described by way of example only with reference to the accompanying drawings, in which.

DETAILED DESCRIPTION OF CERTAIN EMBODIMENTS

Figure 3:
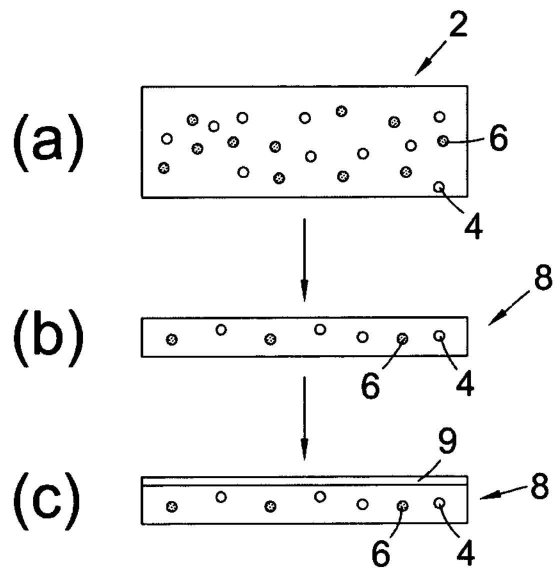
FIG. 3 illustrates a method of fabricating a thin plate of synthetic single crystal diamond material according to an embodiment of the present invention.

FIG. 3 illustrates the basic method of fabricating a thin plate of synthetic single crystal diamond material according to an embodiment of the present invention. A bulk sample of synthetic single crystal diamond material 2 is provided as shown in FIG. 3(*a*). The bulk sample of synthetic single crystal diamond material 2 comprises a plurality of quantum spin defects 4 such as $NV^-$ defect and a plurality of other point defects 6 such as single substitutional nitrogen defects. The concentration of defects is relatively high such that the quantum spin defects cannot be optically isolated. For example, the material may be a synthetic HPHT single crystal diamond material or a synthetic CVD single crystal diamond material.

The bulk sample 2 is then processed to form a thin plate 8 of the synthetic single crystal diamond material as shown in FIG. 3(*b*). The thin plate 8 is made sufficiently thin such that the quantum spin defects 4 can be optically isolated. Furthermore, the plate is made sufficiently thin such that optical absorption across the plate of material is reduced thus increasing the efficiency of excitation of the quantum spin defects and light collection therefrom.

Finally, the plate is treated to form a zero-spin surface termination 9 as shown in FIG. 3(*c*). Typically as-grown CVD synthetic diamond material has a hydrogen terminated surface with nuclear and electron spin. As such, the material must be treated to change the surface termination. For example, an oxygen-terminated diamond surface can be achieved by boiling diamond in concentrated 12 M $H_2SO_4$ saturated with $KNO_3$ for 30 minutes.

In this way, the bulk sample 2 which is not suitable for quantum spin applications may be processed into a thin plate form 8 which is suitable for such applications.

Figure 4:
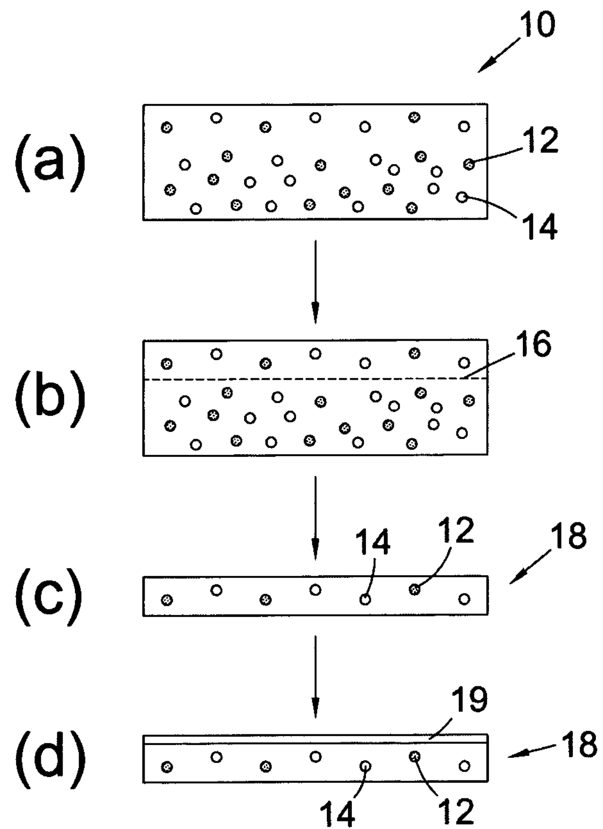
FIG. 4 illustrates in more detail a method of fabricating a thin plate of synthetic single crystal diamond material according to an embodiment of the present invention.

The synthetic single crystal diamond material may be processed into the form of a thin plate using various techniques including one or more of: an implantation and lift off technique; grinding; polishing; and etching. FIG. 4 illustrates an implantation and lift off technique for fabricating a thin plate of synthetic single crystal diamond material. A bulk sample of synthetic single crystal HPHT diamond material 10 is provided as shown in FIG. 4(*a*). The bulk sample of synthetic single crystal HPHT diamond material 10 comprises a plurality of quantum spin defects 14 and a plurality of other point defects 12 as previously described in relation to FIG. 3. Ion implantation is then performed as shown in FIG. 4(*b*) to form an implantation layer 16 defining a thin layer of synthetic single crystal diamond material 18 which can then be removed from the bulk sample as shown in FIG. 4(*c*). Annealing may be used to remove crystallographic damage caused by the processing technique and/or aid in treating the implantation layer 16 to perform lift off. Finally, the thin plate of synthetic single crystal diamond material 18 is treated to provide a zero-spin surface termination 19 as shown in FIG. 4(*d*).

It may be noted that the implantation and release process illustrated in FIG. 4 results in a thin plate of synthetic single crystal diamond material which is formed wholly from the synthetic single crystal diamond material as described herein. This differs from implantation and release processes described in prior art documents such as US2006/0234419, WO2007/009037, and US2005/0181210. These documents describe a CVD growth process in which a substrate is provided with a release layer implanted therein, CVD diamond is grown on the substrate with controlled nitrogen concentration to a target thickness, and then the CVD diamond layer is released via the implanted release layer in the substrate. Substrate implantation and release inevitably leads to a thin layer of substrate material being adhered to the overgrown CVD diamond material. As such, these prior art methods do not appear to disclose a route to a thin plate of synthetic single crystal diamond material which is formed wholly from the synthetic single crystal diamond material as described herein. Furthermore, the prior art methods require growth of the controlled defect diamond material to a target thickness and each plate must be grown and released in separate growth processes. This contrasts with the method illustrated in FIG. 4 which starts from a thick piece of diamond material 10 which is then processed to remove a thin plate 18. The advantage of this method is that it can be repeated to fabricate a plurality of substantially identical plates 18 from a single piece of diamond material 10 without requiring multiple growth runs.

The defect concentration and plate thickness are balanced so that quantum spin defects are optically isolated, have a relatively good decoherence time, and good optical efficiency in terms of excitation and light collection. For example, the plate may have a thickness in a range 100 nm to 50 μm, 500 nm to 30 μm, 1 μm to 20 μm, or 5 μm to 10 μm. The concentration of quantum spin defects may be equal to or greater than 0.1 ppb, 10 ppb, 100 ppb, 1 ppm, 5 ppm, 10 ppm, or 30 ppm. The concentration of quantum spin defects may be equal to or less than 200 ppm, 150 ppm, 100 ppm, or 50 ppm. The aforementioned lower and upper concentration limits may be combined in any manner. For example, the concentration of quantum spin defects may be in a range 0.1 ppb to 200 ppm, 10 ppb to 150 ppm, 100 ppb to 100 ppm, 1 ppm to 50 ppm, or 5 ppm to 50 ppm. In this manner, defect concentration and plate thickness may be controlled such that the optical absorbance at a frequency of 532 nm is low. In certain arrangements, if a thickness value towards the high end of the aforementioned ranges is selected then a concentration value towards the lower end of the aforementioned ranges may be selected to balance these parameters. The concentration of point defects other than the quantum spin defects may be below 200 ppm, 100 ppm, 50 ppm, 20 ppm, 10 ppm, or 5 ppm. In certain arrangements the concentration of such point defects may be as low as possible. However, in practice there will always tend to be some level of such point defects present in the thin plate of synthetic single crystal diamond material. As such, the concentration of these point defects will often be equal to or greater than 0.1 ppb, 0.5 ppb, 1 ppb, or 10 ppb. In certain applications these other point defects may be desirable, for example to form chains linking quantum spin defects in quantum information processing applications.

The density of quantum spin defects may also be defined as a projected planar density as viewed from a direction perpendicular to the thin plate of synthetic single crystal diamond material. For example, projecting the quantum spin defects onto a plane the average projected planar distance between quantum spin defects may be equal to or greater than 500 nm, 1 μm, 2 μm, 5 μm, 8 μm, 10 μm, 20 μm, or 50 μm.

In addition to the above, the synthetic diamond material may be isotopically purified to increase decoherence time of quantum spin defects disposed therein. For example, the synthetic diamond material may have a total concentration of $^{13}C$ equal to or less than 0.9%, 0.7%, 0.4% 0.1%, 0.01%, or 0.001%.

The quantum spin defects may comprise one or more of: a silicon containing defect; a nickel containing defect; a chromium containing defect; and a nitrogen containing defect. While it is envisaged that preferred embodiments will utilize nitrogen containing $NV^-$ defects because of the advantageous properties of this defect as described in the background section, it is also envisaged than certain embodiments of this invention may be applicable to other types of negatively charged defects which are suitable for sensing, detecting and quantum processing applications.

Impurity-vacancy quantum spin defects may be formed by irradiation and annealing. The annealing may be performed during or after irradiation. The annealing may involve heating the diamond material to a temperature equal to or greater than 600° C., 700° C., 800° C., 900° C., 1000° C., or 1200° C. Alternatively, impurity-vacancy quantum spin defects may be formed during growth of the diamond material rather than using post-growth treatments such as irradiation and annealing.

For example, the total nitrogen concentration may be equal to or greater than 10 ppm, 20 ppm, 50 ppm, 100 ppm, 150 ppm, 200 ppm, 250 ppm, 300 ppm, 400 ppm, or 600 ppm where all other point defects are equal to or less than 1/10, 1/100, or 1/1000 of these levels. Such material provides a route (through irradiation and annealing or otherwise) to produce synthetic diamond material containing a concentration of $NV^-$ defects equal to or greater than 0.1 ppm, 1 ppm, 5 ppm, 10 ppm, 25 ppm, 50 ppm, 100 ppm, or 200 ppm.

In addition to controlling the concentration of point defects within the synthetic diamond material, it is also advantageous to ensure that the concentration of extended crystallographic defects such as dislocations defects is low so as to improve optical properties of the thin plate (e.g. reduce birefringence) and so as to reduce strain in the thin plate which can reduce the decoherence time of the quantum spin defects. Accordingly, the thin plate of synthetic single crystal diamond material may have one or more of the following characteristics:

(1) a birefringence in a direction perpendicular to the thin plate of synthetic single crystal diamond material equal to or less than $5\times10^{-5}$, $1\times10^{-5}$, $5\times10^{-6}$, or $1\times10^{-6}$;

(2) a density of extended defects as characterised by X-ray topography equal to or less than 400 per $cm^2$, 300 per $cm^2$, 200 per $cm^2$, or 100 per $cm^2$;

(3) a FWHM ("Full Width at Half Maximum") X-ray rocking curve width for a (004) reflection equal to or less than 50 arc seconds, 20 arc seconds, 10 arc seconds, 7 arc seconds, 5 arc seconds, 3 arc seconds, 2 arc seconds, or 1.5 arc seconds.

As used herein, the term "extended defects" refers to defects such as dislocations or dislocation bundles and stacking faults.

In certain arrangements, device performance may be limited due to the excitation and collection efficiency of the quantum spin defects. For instance the present defects (N, NV) lead to a reduction in the light excitation and also self-absorption limits the collected luminescence. In this case it can be desirable to produce a large area plate (consistent with increasing the number of NV defects) which is optically thin. In such an arrangement, even though the defect concentration may be such that decoherence time of the quantum spin defects is not at its peak value, the number of quantum spin defects and the optically efficiency of the quantum spin defects is such that a reduced decoherence time is compensated.

In certain other arrangement is can be desirable to have a lower concentration of defects to produce a layer where individual quantum spin defects can more readily be addressed using optical techniques such as confocal microscopy, Stimulated Emission Depletion (STED) microscopy, or Fluorescence Lifetime Imaging Microscopy (FLIM) while ensuring that decoherence times are long. In essence, this puts certain restrictions on the lateral, and optionally vertical, spacing of the quantum spin defects. By thinning a plate it is possible to isolate single quantum spin defects in the z direction. In such arrangements, the quantum spin defects may have a decoherence time $T_2$ equal to or greater than 0.05 ms, 0.1 ms, 0.3 ms, 0.6 ms, 1 ms, 5 ms, or 15 ms, with corresponding $T_2^*$ values equal to or less than 400 μs, 200 μs, 150 μs, 100 μs, 75 μs, 50 μs, 20 μs, or 1 μs. Furthermore, the product of the concentration of quantum spin defects and decoherence time $T_2$ is preferably at least 0.1 ppm μs, 1 ppm μs, 10 ppm μs, 20 ppm μs, 30 ppm μs, 50 ppm μs, 100 ppm μs, 200 ppm μs, 500 ppm μs, 1000 ppm μs, or 5000 ppm μs.

The specific size and dimensions of the thin plate of single crystal synthetic diamond material will to some extent be dependent on the device configuration and its intended use. However, for many applications the plate of single crystal synthetic diamond material may need to be sufficiently large to contain enough quantum spin defects to improve sensitivity while the distribution of the quantum spin defects is sufficiently dispersed to improve the decoherence time of the point defects and/or make it possible to isolate single defect centres using optical techniques. The fact that the plate is thin is advantageous as the quantum spin defects will all be positioned relatively close to a surface of the plate which can increase sensitivity to changes in the magnetic or electric field adjacent the surface.

A thin plate of synthetic single crystal diamond material as previously described can be used to fabricate a component for a sensor, detector or quantum processing device. To form such a component, the thin plate of synthetic single crystal diamond material can be mounted on a supporting substrate. For optical applications the supporting substrate may be optically transparent such that light may pass through the supporting substrate for excitation of the quantum spin defects or for collection of light emitted therefrom. Alternatively, the supporting substrate may comprise an optically reflective structure such that optical excitation and detection may be performed from the same side of the thin plate of synthetic single crystal diamond material, light passing through the thin plate and then reflected back through the thin plate from the optically reflective structure in the supporting substrate. The optically reflective structure may, for example, comprise a Bragg reflector.

An out-coupling structure may be formed at or near a surface of the thin plate of single crystal synthetic diamond material for increasing out-coupling of light and increasing light collection from quantum spin defects in the synthetic diamond material. Suitable out-coupling structures include one or more of: a convex surface; a microlens array; a solid immersion lens (SIL); a plurality of surface indentations or nano-structures; a diffraction grating; a fresnel lens; and a coating such as an antireflective coating. The out-coupling structure may be formed in the supporting substrate.

It is also desirable to process a surface of the thin plate of diamond material so as to achieve a low surface roughness Rq. As described in WO 2010010344 and WO 2010010352, high $T_2$ values and high spectral stability can be obtained using the synthetic diamond material of the present invention as a host material where the quantum spin defect is to be positioned at a distance of equal to or less than 100 μm from such a processed surface. According to embodiments of the present invention the quantum spin defects may optionally be positioned at a distance of equal to or less than 100 μm, preferably 50 μm, preferably 20 μm, preferably 10 μm, preferably 1 μm, preferably 500 nm, preferably 200 nm, preferably 50 nm, preferably 20 nm, or preferably 10 nm from such a processed surface. This positioning of the quantum spin defect means that it is readily accessible for end applications such that it can be characterised and "read out", for example, by optical coupling to a waveguide. Thus, it is advantageous to form a quantum spin defect in the quantum grade single crystal diamond, wherein a surface of the diamond material is processed such that the surface roughness, Rq of the single crystal diamond within an area defined by a circle of radius of about 5 μm centred on the point on the surface nearest to where the quantum spin defect is formed is equal to or less than about 10 nm, 5 nm, 1 nm, or 0.5 nm.

In additional to low surface roughness at a surface near a quantum spin defect, it is also useful to ensure that subsurface damage is low near a quantum spin defect. Subsurface damage may be reduced by etching, such as with a plasma etch, after polishing and prior to treating the surface to achieve a suitable zero-spin surface termination.

Figure 5:
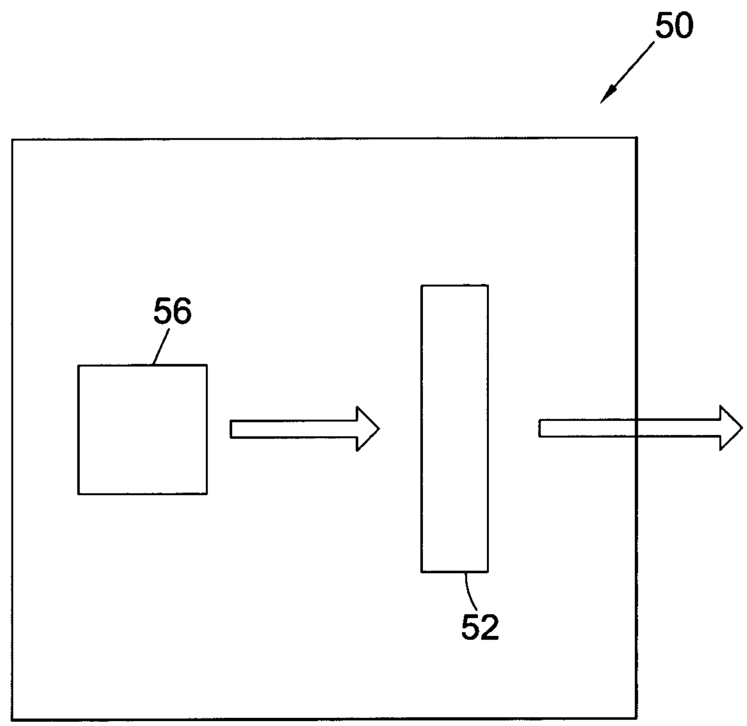
FIG. 5 shows a schematic diagram of a spin resonance device according to an embodiment of the present invention.

Synthetic diamond device components as previously described can be used to form a diamond quantum device. An example of such a device is illustrated in FIG. 5. The quantum device 50 comprises a diamond quantum component 52 comprising a thin plate of single crystal synthetic diamond material as previously described, optionally supported by a substrate. The quantum device also comprises a light source 56 for optically pumping one or more of the plurality of quantum spin defects in the thin plate of single crystal synthetic diamond material.

Figure 1A:
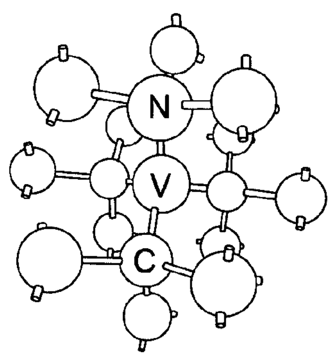
FIG. 1*a* illustrates the atomic structure of an $NV^-$ defect.

The light source 56 is tuned to an appropriate frequency to excite the quantum spin defects into undergoing an electron transition as illustrated in FIG. 1(*a*). The electronic structure of the defect allows the defect to be optically pumped into its electronic ground state allowing such defects to be placed into a specific electronic spin state even at non-cryogenic temperatures. This can negate the requirement for expensive and bulky cryogenic cooling apparatus for certain applications where miniaturization is desired. Further transitions and subsequent decay and fluorescent emission will result in the emission of a photon which all having the same spin state. As such, this device configuration can function as a source of photons which all having the same spin state which is useful for further quantum processing applications based on photonics.

In configuring components and devices comprising a thin plate of synthetic single crystal diamond material as described herein, it will be appreciated from the previous discussion that there are substantial benefits to isolating quantum spin defects from coupling interactions which reduce decoherence time. As such, in addition to careful design, fabrication, and processing of the thin plate of synthetic single crystal diamond material to reduce such detrimental interactions, certain components and devices may be configured to ensure that the environment surrounding the thin plate of synthetic single crystal diamond material does not detrimentally affect the functional performance of the material. As such, components and devices may be configured to ensure that the thin plate of synthetic single crystal diamond material is mounted in a vacuum or in a controlled gaseous environment comprising one or more selected gases which are not spin active. Such an arrangement can ensure that the environment immediately surrounding the thin plate does not adversely affect the quantum spin defects. Such an arrangement is desirable when the device is designed to use the quantum spin defects to sense external changes beyond the immediate surrounds of the thin plate. Alternatively, certain other components and devices may be configured specifically to sense the environment immediately surrounding the thin plate. For example, the device may be configured to locate a sample of material adjacent the thin plate for performing sensing operations thereon, e.g. at least a portion of the thin plate may be exposed to, or immersed in, a fluid or gas of interest for analysis.

Figure 6:
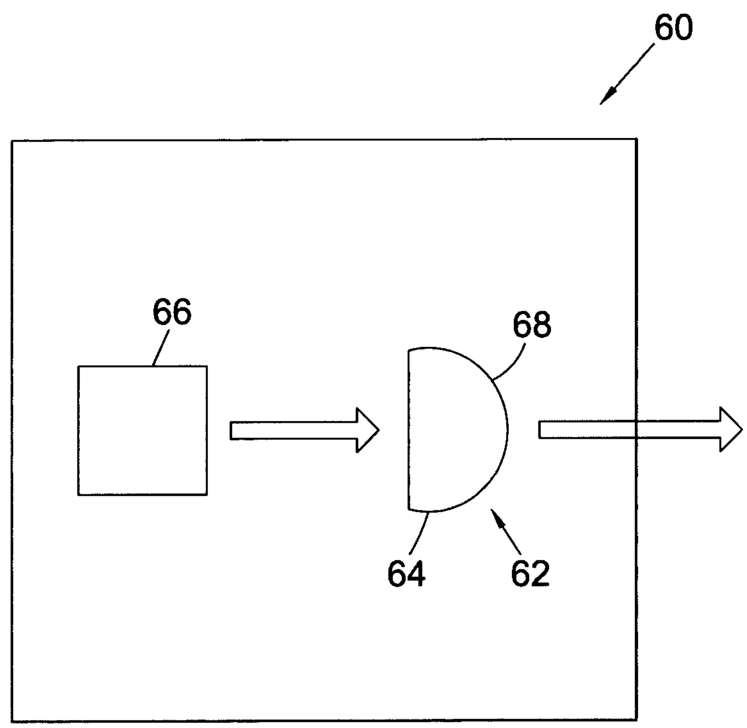
FIG. 6 shows a schematic diagram of a spin resonance device according to another embodiment of the present invention.

FIG. 6 shows a similar diamond quantum device 60. This device 60 also comprises a diamond quantum component 62 including a thin plate of single crystal synthetic diamond material 64 as previously described. The quantum device also comprises a light source 66 for optically pumping one or more of the plurality of quantum spin defects in the layer 64.

The diamond quantum device 60 shown in FIG. 6 differs from that shown in FIG. 5 in that the diamond component 62 has been formed to have an out-coupling structure 68 to increase light output from the emitting quantum spin defects in the thin plate of synthetic single crystal diamond material.

Figure 7:
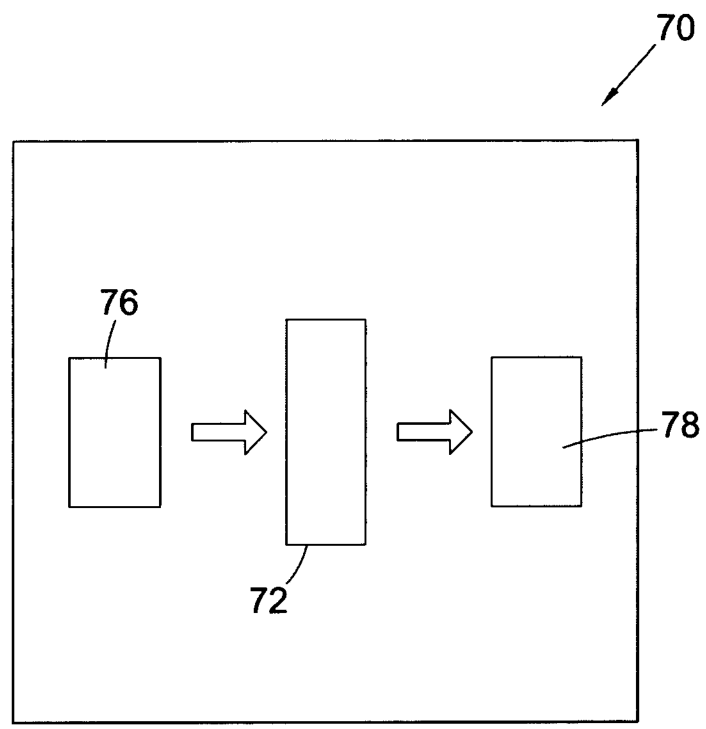
FIG. 7 shows a schematic diagram of a spin resonance device according to another embodiment of the present invention.

FIG. 7 shows another example of a diamond quantum device 70. This device includes a diamond quantum component 72 and a light source 76 as previously described. The device 70 differs from that illustrated in FIGS. 5 and 6 in that it further comprises a detector 78 for detecting emission from one or more decaying quantum spin defects 74 in the diamond quantum component 72.

In this device configuration, any perturbation of the $NV^-$ defects which results in an electron transition to a $m_s=\pm1$ state will result in a reduction in fluorescent emission which can then be detected by the detector 78.

Figure 8:
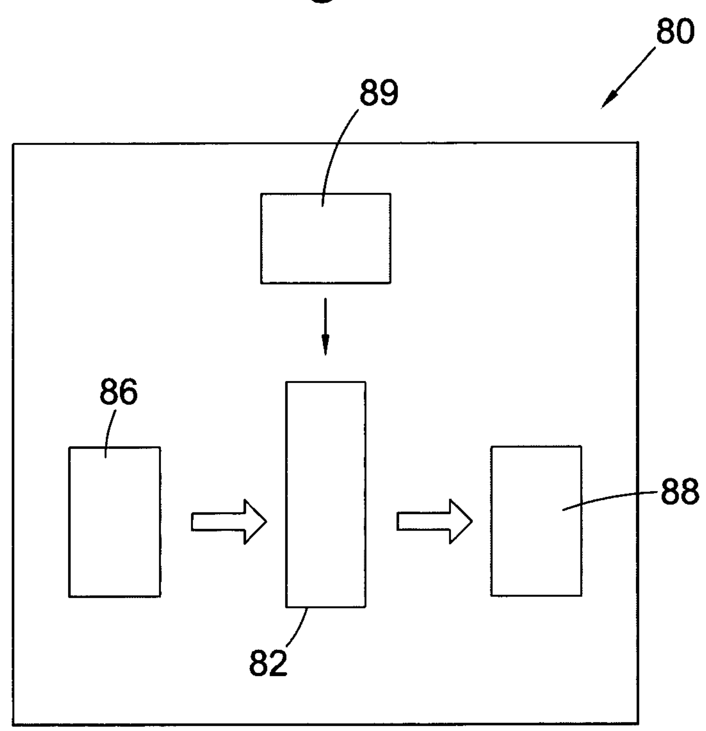
FIG. 8 shows a schematic diagram of a spin resonance device according to another embodiment of the present invention.

FIG. 8 shows another example of a diamond quantum device 80. This device includes a diamond quantum component 82 and a light source 86 as previously described. The device 80 also comprises a detector 88 for detecting emission from one or more decaying quantum spin defects 84 in the diamond component 82. The device 80 differs from that illustrated in FIG. 7 in that it further comprises a microwave generator 89 for manipulating one or more of the plurality of quantum spin defects in the single crystal synthetic diamond plate.

In this device configuration, the diamond quantum device can function as a magnetometer, the microwave generator 89 being configured to scan a range of microwave frequencies for manipulating one or more of the plurality of quantum spin defects in the single crystal synthetic diamond component 82. At a certain frequency the $NV^-$ defects will undergo an electron transition from the $m_s=0$ to an $m_s=\pm1$ state resulting in a decrease in the fluorescent emission from the $NV^-$ defects. The frequency at which this transition will occur will depend on the energy level of the $m_s=\pm1$ states which will be perturbed by an external magnetic or electric field. As such, the frequency at which a decrease in fluorescent emission occurs can be used to measure an external magnetic or electric field.

In a modified version of the device shown in FIG. 8, the device may also comprise a static field generator to split the degeneracy of the $m_s=\pm1$ states, the magnitude of this splitting then being perturbed by any external magnetic or electric field leading to a change in the frequency at which a decrease in fluorescent emission occur, this change corresponding to a change in magnitude and/or direction of an external magnetic or electric field.

Alternatively, the diamond quantum device illustrated in FIG. 8 may be configured to function as a quantum information processing device. In such an arrangement, the microwave generator 89 can be configured to selectively manipulate the plurality of quantum spin defects in the single crystal synthetic diamond component in order to write information to the plurality of quantum spin defect and the detector 88 can be configured to selectively address one or more of the plurality of quantum spin defects in order to read information from the plurality of quantum spin defects.

Figure 9:
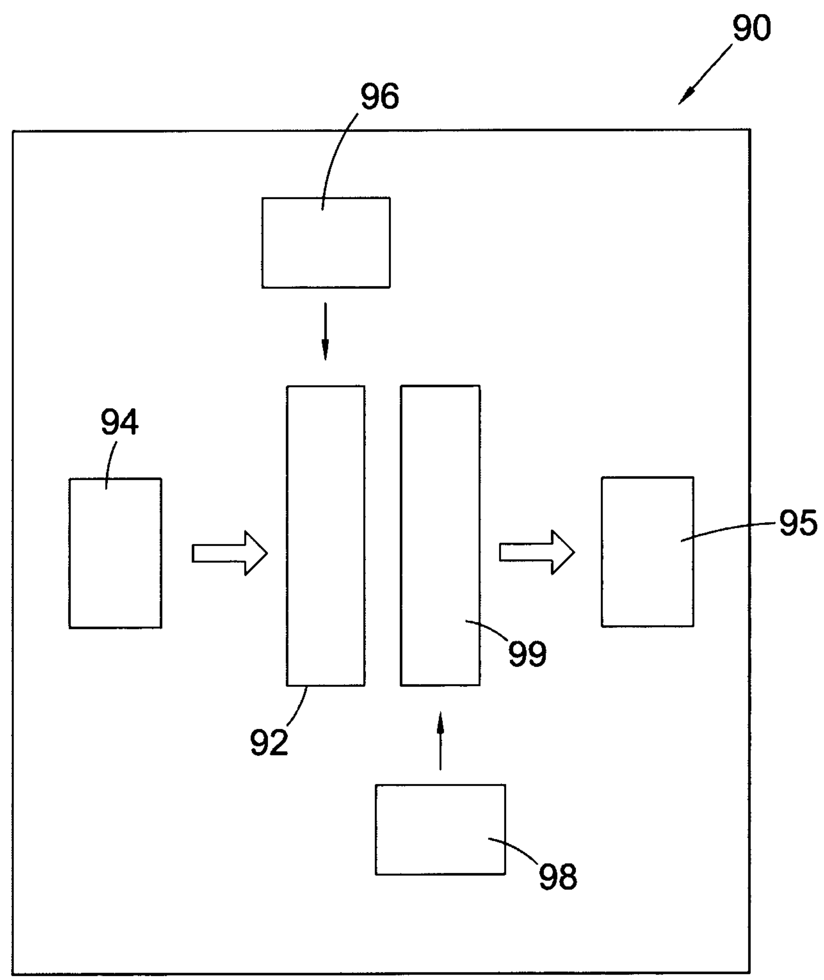
FIG. 9 shows a schematic diagram of a spin resonance device according to another embodiment of the present invention.

FIG. 9 shows another example of a diamond quantum device 90. This device includes a diamond component 92. The device 90 also comprises a detector 95 for detecting emission from one or more decaying quantum spin defects in the single crystal CVD synthetic diamond component 92 and a microwave generator 96 for manipulating one or more of the plurality of quantum spin defects in the single crystal synthetic diamond component. The microwave generator 96 is configured to scan a range of microwave frequencies for manipulating one or more of the plurality of quantum spin defects in the single crystal synthetic diamond plate. The device 90 further comprises a radio or microwave frequency generator 98 configured to scan a range of frequencies for manipulating quantum spins within a sample 99 disposed adjacent the diamond component 92.

This device configuration can function as a spin resonance device. Such a device may also comprise a static field generator. In such an arrangement, the sample 99 is subjected to a static field, e.g. a static magnetic field. By applying a static magnetic field to the sample 99, the spins of nuclei within the sample are preferentially aligned with the applied magnetic field. An oscillating field is then applied to the sample and the frequency varied. When the oscillating field comes into resonance with a nuclear spin it flips the nuclear spin to be oriented against the direction of the static field. This transition leads to a change in the local magnetic field which can be sensed and detected. Different nuclei will spin-flip at different frequencies of the applied oscillating field due to local shielding effects of surrounding electrons and spin-spin interactions between closely spaced nuclear spins.

So far, the described device functions like a standard NMR device but with a much smaller sample volume and a much lower static field allowing the use of, for example, a small magnet (or indeed no magnet if the earth's magnetic field is used) and thus allowing miniaturization of the device as a whole. In contrast to a standard NMR device, changes in the local magnetic field resulting from nuclear spin flipping are detected using one or more quantum spin defects disposed in the thin plate of single crystal synthetic diamond 92 adjacent the sample 99.

Figure 1B:
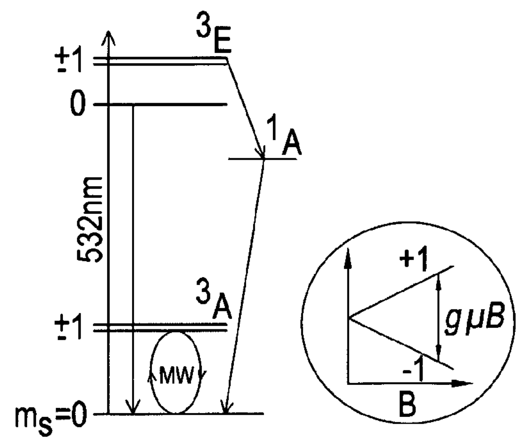
FIG. 1*b* illustrates the electronic structure of an $NV^-$ defect.
Figure 2A:
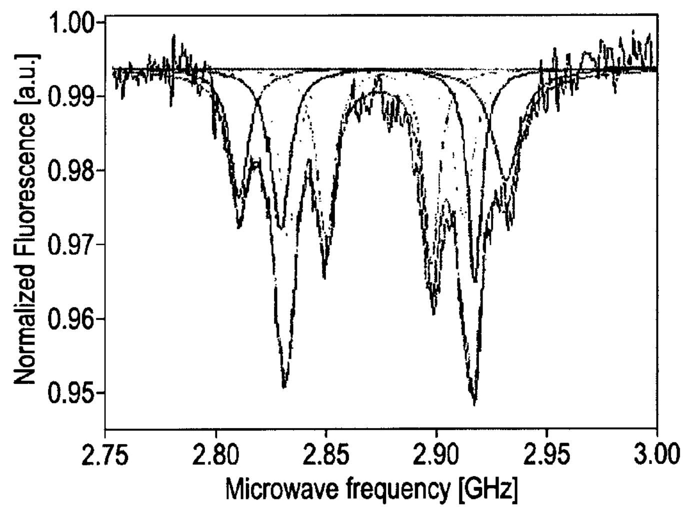
FIG. 2*a* illustrates a characteristic fluorescence spectrum obtained from a plurality of $NV^-$ defects manipulated by a varying microwave frequency.
Figure 2B:
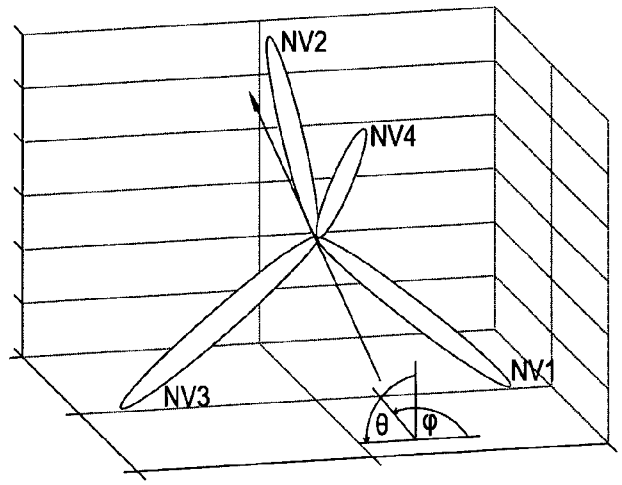
FIG. 2*b* illustrates the orientation of four crystallographic $NV^-$ axes in a diamond crystal.

$NV^-$ defects are disposed within the previously described static magnetic field. Accordingly, the degeneracy of the electron spin states $m_s=\pm1$ within the $NV^-$ defects is split as illustrated in FIG. 1*b*. The $NV^-$ defects are excited with an optical laser source at 532 nm causing excitation of electrons from the $^3A$ ground state to the $^3E$ excited state. The excited $m_s=0$ electrons fluoresce on transition back to the ground state emitting and this fluorescence is detected. An oscillating microwave field is applied to the $NV^-$ defects and the frequency varied. When the oscillating microwave field comes into resonance with the electron spin of an $NV^-$ centres it causes an electron to undergo a transition to $m_s=\pm1$ state. The resonant spin transitions can be probed by sweeping the microwave (MW) frequency resulting in characteristic dips in the optically detected magnetic resonance (ODMR) spectrum as previously described by Steinert et al. with reference to FIG. 2a.

Now, the energy of the $m_s=\pm1$ state will be dependent on the static field but will be perturbed by local variations in the magnetic field caused by the nuclear spin flipping in the sample induced by the oscillating field. As such, the microwave frequency at which electron spin resonance will occur in the $NV^-$ defects will be shifted when nuclear spins in the sample come into resonance with the oscillating field. These changes are detected by a shift in the dip at which fluorescence occurs. As such, nuclear spin resonance in the sample is optically detected via changes in the electron spin resonance in the $NV^-$ defects. The optical signal can thus be processed to generate NMR data. This may be in the form of an NMR spectrum indicating chemical shift data. Alternatively, or additionally, a magnetic resonance image (MM) can be generated for a sample if a plurality of optical readings are taken at different positions of the sample. In such a spin resonance imaging device, the detector can be configured to spatially resolve emission from the plurality of quantum spin defects in the single crystal synthetic diamond component to form a spin resonance image. Alternatively, or additionally, changes in the electric field can be measured using this technique.

Data generated using the aforementioned processed may be displayed on a display screen of the device. Alternatively, data may be transmitted, either wired or wirelessly, to an external device such as a laptop or desktop computer for processing and display. In this case, the processing and display within the quantum device can be simplified and reduced in size and cost. A suitable computer program can be provided to run on a standard computer for receiving, processing and displaying data gathered by a portable quantum device.

A quantum device as previously described may be configured to be a microfluidic device comprising a microfluidic channel for receiving a fluid sample, the single crystal synthetic diamond component being located adjacent the microfluidic channel. In such an arrangement, the microfluidic channel and the single crystal synthetic diamond component acting as a quantum sensor can be integrated into a microfluidic cell such as that illustrated in FIG. 10.

Figure 10:
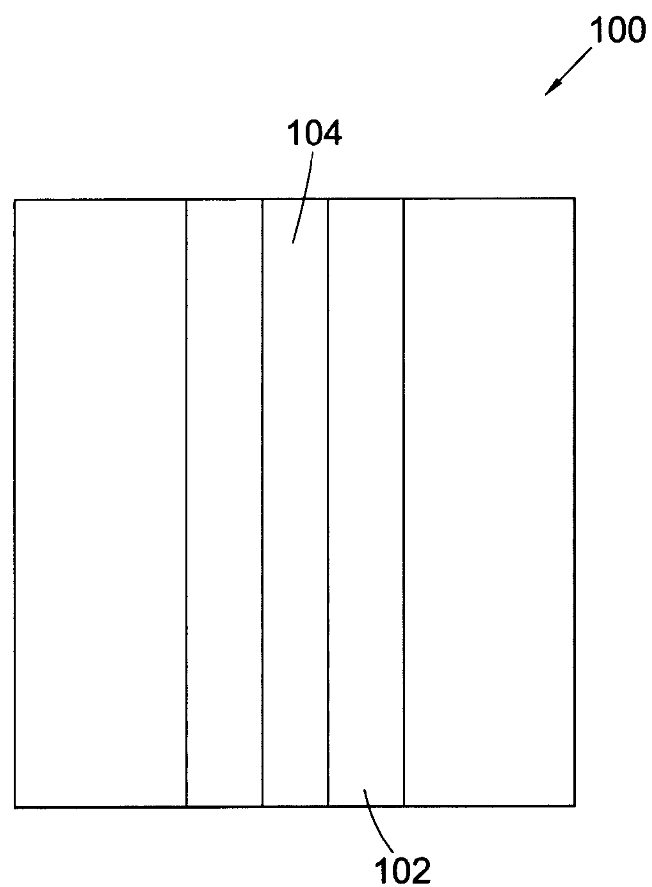
FIG. 10 shows a schematic diagram of a microfluidic cell comprising a layered synthetic single crystal diamond material for use in a diamond quantum device according to an embodiment of the present invention.

FIG. 10 shows an example of a diamond based microfluidic cell 100. The microfluidic cell 100 comprises at least one diamond sensor 102 positioned adjacent a channel 104 into which a fluid sample can be disposed. The at least one diamond sensor 102 comprises one or more quantum spin defects 106 which may be formed using the thin plate as previously described. The diamond sensor 102 is positioned adjacent the channel 104 to sense changes in the magnetic and/or electric field within a sample located in the channel 104. The illustrated arrangement comprises two diamond sensing elements 102 placed on opposite sides of the channel 104. However, it is envisaged that the microfluidic cell may comprise only one or alternatively a plurality of diamond sensing elements.

The microfluidic channel preferably has at least one dimension equal to or less than 1 mm, more particularly in the range 100 nm to 1 mm, optionally in the range 500 nm to 500 μm. The size of the microfluidic channel may be chosen to be selective of certain species. More than one channel may be provided. The different channels may have different sizes to be selective of different species based on differences in the size of the species.

Figure 11:
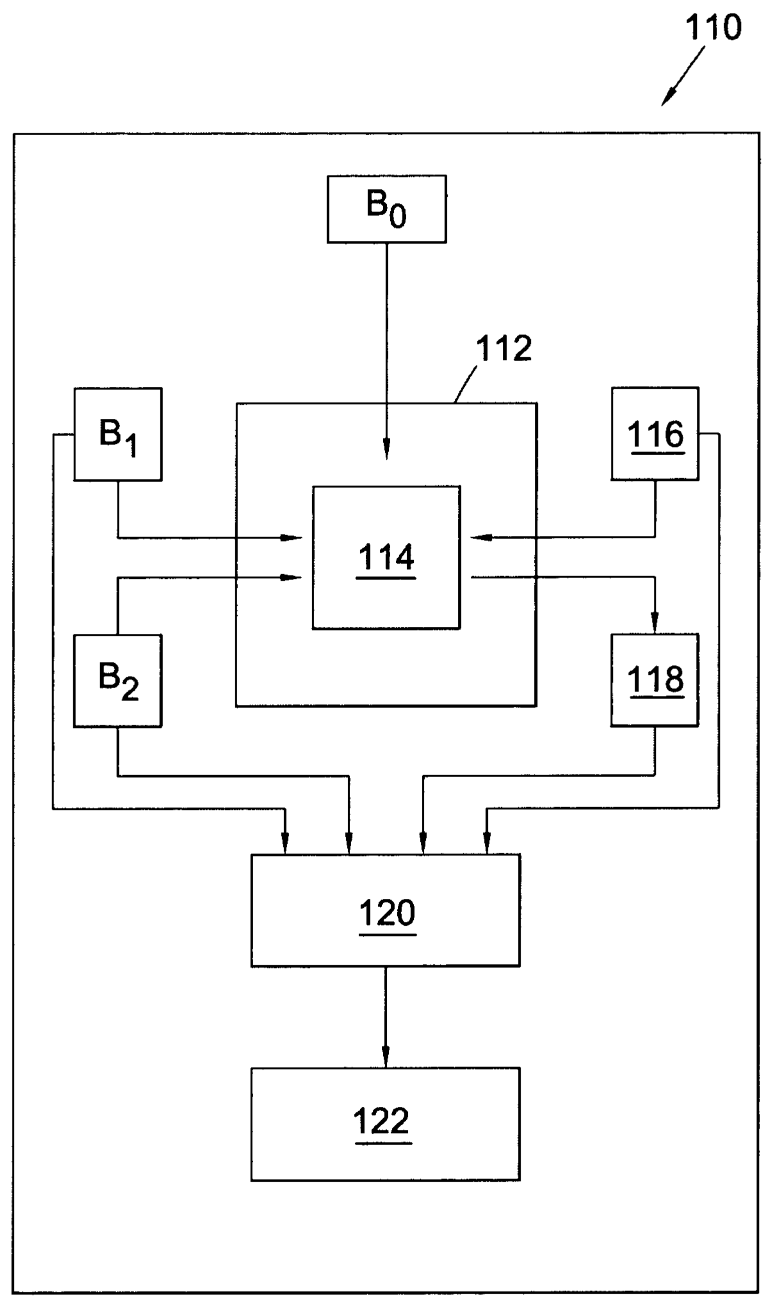
FIG. 11 shows a schematic diagram of a spin resonance device for use with a microfluidic cell such as that illustrated in FIG. 10.

FIG. 11 shows a spin resonance device 110 for use with a microfluidic cell such as that shown in FIG. 10. The device 110 comprises a static magnetic field generator ($B_0$), a first variable oscillating magnetic field generator ($B_1$) and a second variable oscillating magnetic field generator ($B_2$). The first variable oscillating magnetic field generator ($B_1$) is preferably a radio frequency generator and the second oscillating variable magnetic field generator ($B_2$) is preferably a microwave generator. The device may further comprise magnetic shielding 112 disposed around a cell receiving bay 114. In one arrangement the earth's magnetic field is used as a static magnetic field and thus no additional static magnetic field generator is required. In such an arrangement, the shielding may be adapted to shield the sensor from any external oscillating fields but not against a static magnetic field. Such shielding is known to those skilled in the art. The spin resonance device also comprises a light source 116 configured to excite quantum spin defects in a diamond based microfluidic cell mounted in the cell receiving bay 114 and an optical detector 118 for detecting optical output signals from the quantum spin defects in the diamond based microfluidic cell. The light source may be a laser light source. The light source may be configured to selectively excite quantum spin defects at different positions along the microfluidic channel to allow analysis of fluid at different positions along the channel. Alternatively or additionally, the detector may be configured to selectively detect emission from quantum spin defects at different positions along the microfluidic channel to allow analysis of fluid at different positions along the channel.

In an alternative arrangement, the previously described magnetic field generators may be replaced with electric field generators. The electronic structure of the $NV^-$ defect is such that embodiments of the present invention can also be used to measure electric fields as an alternative to, or in addition to, magnetic fields.

One or more processors 120 may be disposed within the spin resonance device and linked to the detector 118 to receive and process emission data. The one or more processors 120 may be linked to an output 122 for outputting results. The output 122 may comprise a display screen for displaying spin resonance data. The one or more processors 120 and the display 122 may be integrated into the spin resonance device. Alternatively, or additionally, the output 122 may be adapted for transmitting data to an external device such as a laptop or desktop computer for processing and displaying data.

Such a device can function as previously described in relation to FIG. 9. A suitable pulse sequence may be selected and utilized to increase decoherence time. As such, the devices previously described may be configured to impart a pulsed signal to the one or more quantum spin defects to increase decoherence time and thus improve sensitivity. A typical pulse sequence would comprise a $\pi/2$ pulse followed by a $\pi$ pulse followed by another $\pi/2$ pulse.

Example

Preparation and Mounting of Thin Film

A type 1b synthetic HPHT diamond containing a nitrogen concentration of [N]<100 ppm was provided. In PL experiments under 532 nm excitation the neutral)($NV^0$) and negatively charged ($NV^-$) nitrogen-vacancy defects were the only colour centres detected in the sample. In the HPHT bulk sample a high density of such defects were observed, and individual colour centres could not be resolved.

A film of 1 μm thickness was defined by implantation of He ions at an energy of 0.5 MeV and a fluence of approximately $5\times10^{16}$ ions/cm$^2$, followed by annealing in a forming gas (Ar, 4% $H_2$) for one hour at 800° C. To grant access to the graphite layer, a focused-ion beam (FIB) of 30 keV $Ga^+$ ions was used to drill 5 μm holes to a depth of 2 μm. The film was then undercut using a cycle of galvanic etches to remove the graphite layer. Once the graphite had been removed, a final clean in oxidizing acids removed any non-sp$^3$ carbon. A further FIB milling process was then used to define an approximately square film of 60 to 80 μm side length.

To separate the film from a supporting substrate a micromanipulator probe was then attached with a platinum weld, before a final cut with FIB released the layer from the substrate. The thin layer/plate was then lifted out and transferred to a different substrate. In particular, the thin plate sample was bonded to an optically flat substrate with platinum spot-welds and the manipulator tip cut free. The optically flat substrate was composed of a silica plate coated with 8 pairs of $\lambda/4$ $SiO_2/TiO_2$ forming a distributed Bragg reflector with peak reflectivity of 99.5% at a centre wavelength of 637 nm.

Scanning Confocal Microscopy

Optical characterisation of the film at room temperature and 77K was performed using a scanning confocal microscope. Optical excitation of the sample for PL and Raman spectroscopy was carried out using a 532 nm diode pumped solid state laser, and a 637 nm semiconductor diode laser, while illumination for reflectance spectroscopy was with a calibrated tungsten filament white-light source. Optical detection for imaging purposes was with a silicon photon counting module, while for spectrally-resolved data a $LN_2$-cooled CCD camera was used on a 0.75 m imaging spectrometer with a 300 lines/mm grating. To study the flatness of the film mounted on the substrate, reflectance imaging was performed at a peak reflectivity wavelength of the mirror of 637 nm.

Spectroscopy

Figure 12:
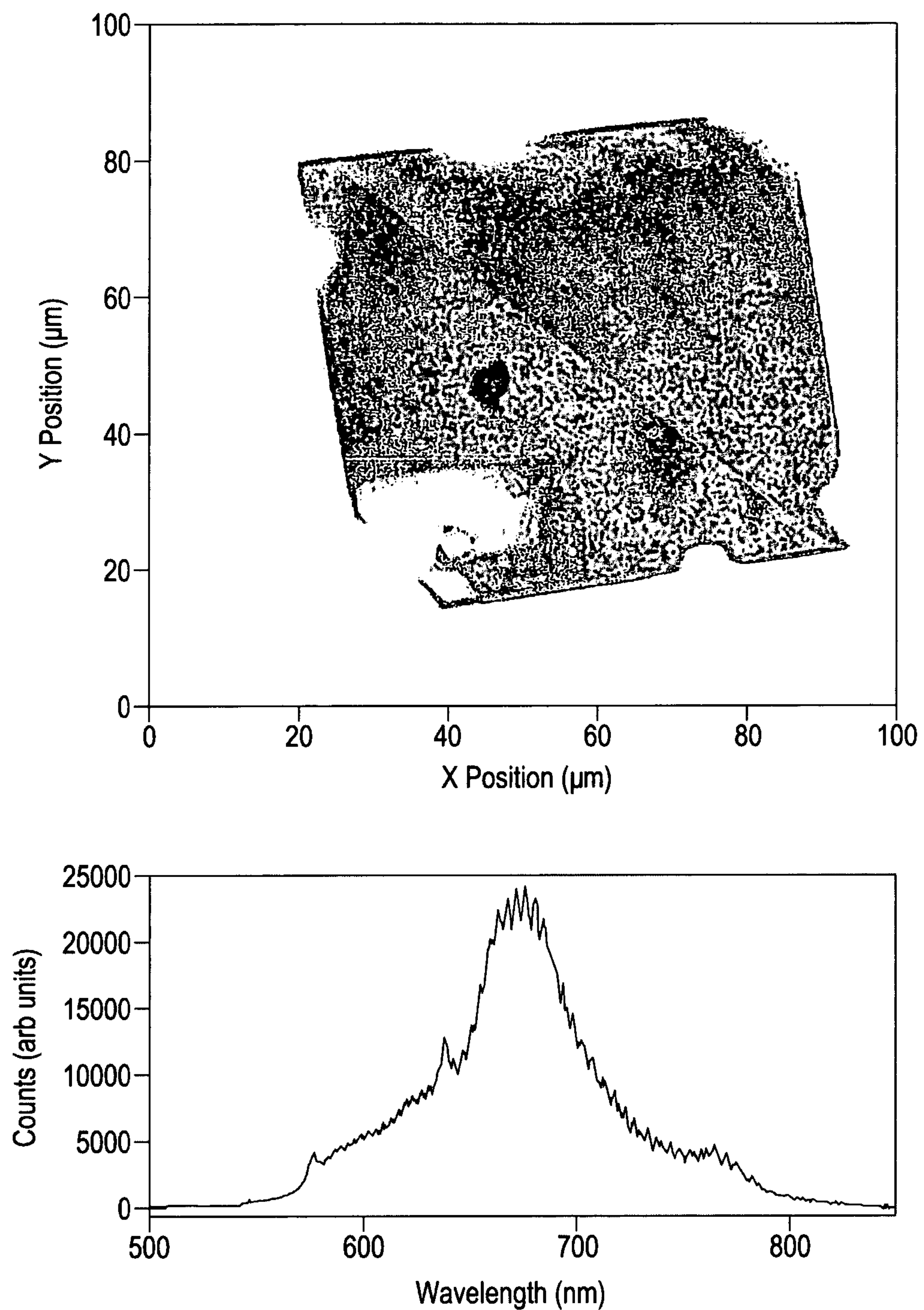
FIG. 12 shows a room temperature PL image and spectrum from a synthetic HPHT thin-film diamond with a relatively large concentration of NV centres.

In the HPHT thin-film sample, a high concentration of NV centres in the source material guarantees the presence of a large number of colour centres within the film. FIG. 12 shows a room temperature PL image and spectrum from this sample. In the PL image a twinning dislocation is visible as a diagonal line across the sample. In the bottom left corner, strong suppression of the PL signal is apparent, resulting from the FIB exposure required to attach the micromanipulator tip for separation of the film from the substrate.

Figure 13:
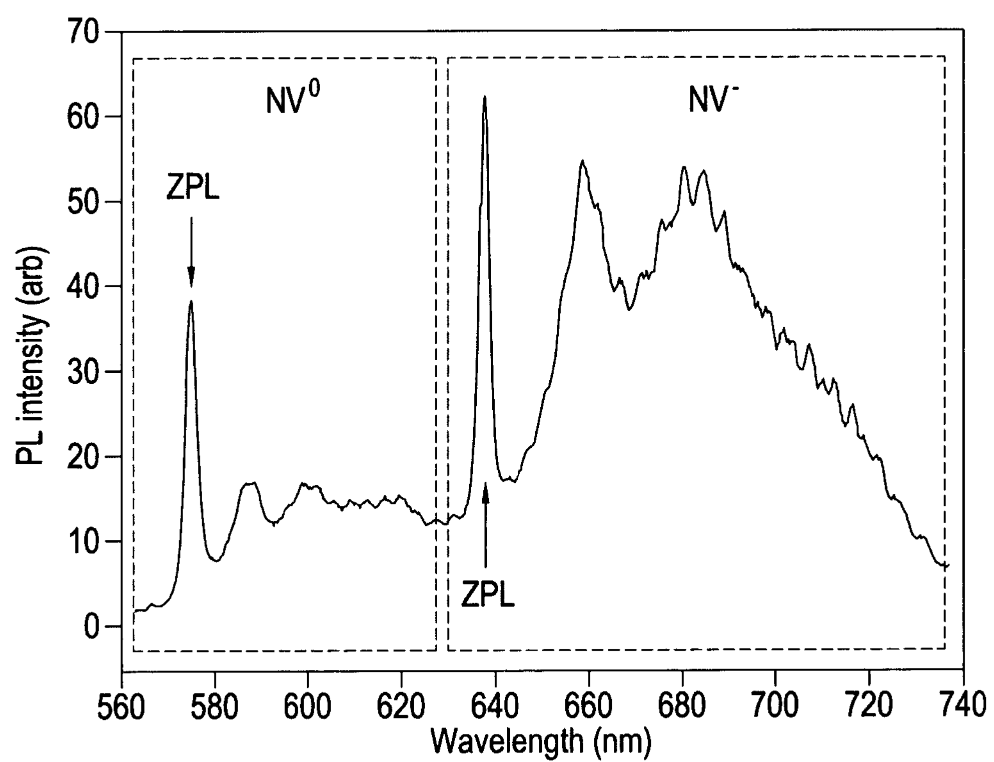
FIG. 13 shows a low temperature (77 K) spectrum from the synthetic HPHT thin-film diamond with emission from both $NV^-$ and $NV^0$ being observed.

The spectrum in the lower portion of FIG. 12 reveals strong NV-centre emission, with the zero phonon line (ZPL) at 637 nm from the $NV^-$ charge state clearly visible. Also visible is some contribution from $NV^0$, with its ZPL visible at 575 nm. These ZPLs, and their corresponding vibronic sidebands, are seen much more clearly in the 77K spectrum in FIG. 13.

White Light Imaging and Reflectance

Figure 14:
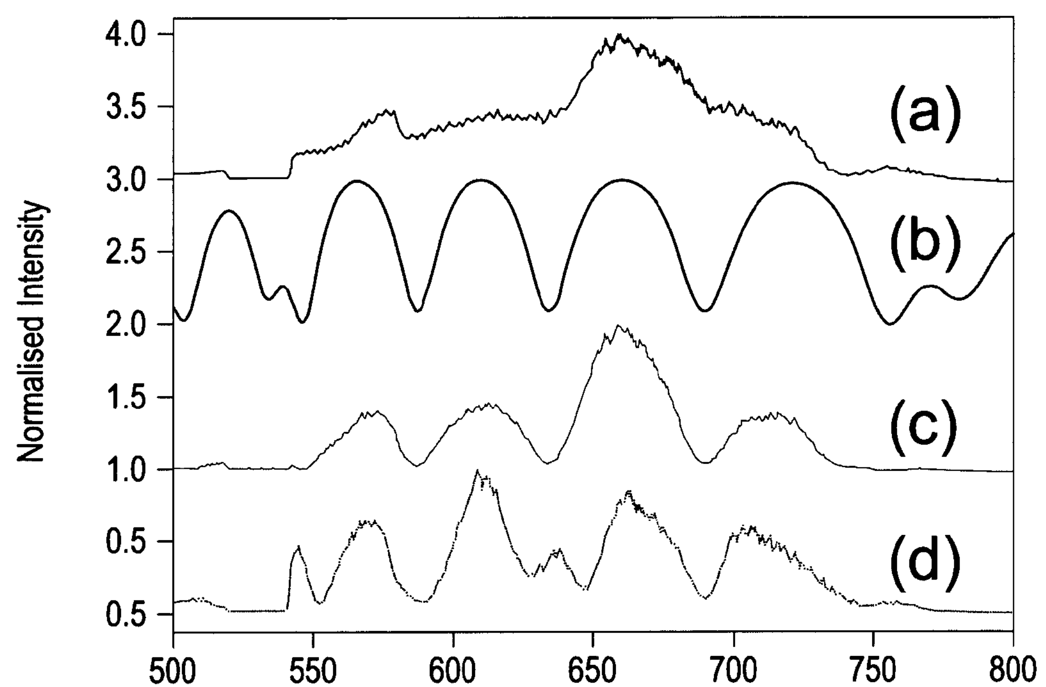
FIG. 14 shows white-light reflectance spectra of the synthetic HPHT thin-film diamond: (a) measured intensity spectrum of the white light source; (b) calculated reflection spectrum for the synthetic HPHT thin-film diamond; (c) modelled reflectance for the synthetic HPHT thin-film diamond; and (d) measured reflectance from the synthetic HPHT thin-film diamond.

Further information on the optical quality of the thin-film was obtained by performing reflectance spectroscopy using a white-light source coupled into the microscope. FIG. 14(*d*) shows a typical reflectance spectrum taken from the HPHT sample. The observed periodic modulation is attributed to the existence of Fabry Perot modes in the thin film, whereby the minima in reflectance correspond to the mode wavelengths where light penetrates the film and is lost instead of being reflected from the top surface. A one-dimensional transfer matrix approach was used to simulate the experiment and to attempt to better quantify the magnitude of these losses. The free parameters are the thickness of diamond L, and a round-trip loss coefficient $\gamma$. The thickness of the diamond from the observed free-spectral range of the reflectivity peaks was chosen taking account of the bulk refractive index of diamond n=2.4. The Bragg-stack reflector is also fully modelled so that field penetration into the mirror is included. FIG. 14(*a-c*) shows the results of this analysis, with FIG. 14(*a*) being the spectrum of the white-light source, (b) the calculated reflectivity spectrum and (c) the spectrum after correction for the spectrum of the excitation source. As can be seen from comparison of FIGS. 14(*c*) and (*d*), there is a good agreement between the observed reflectivity and the model. In order to match the peak modulation, $\gamma$=0.8 was required. It is interesting to note that in the experimental data a peak is observed at about 637 nm, which was attributed to luminescence from $NV^-$ in this film.

CONCLUSIONS

In the pursuit of high quality diamond films containing isolated colour centres, this example has demonstrated the retention of bright NV luminescence in a thin plate of synthetic single crystal HPHT diamond after an implantation and lift-off process used to form the thin plate. Such thin plates have good optical characteristics for efficient excitation of quantum spin defects and collection of light emitted by the excited quantum spin defects. Such thin plates may thus be utilized in sensing, detecting and quantum information processing as an alternative to thicker samples of very high purity synthetic CVD diamond material.

While this invention has been particularly shown and described with reference to preferred embodiments, it will be understood to those skilled in the art that various changes in form and detail may be made without departing from the scope of the invention as defined by the appendant claims.

The invention claimed is:

1. A thin plate of synthetic single crystal diamond material, the thin plate of synthetic single crystal diamond material having:

a thickness in a range 100 nm to 50 μm;

a concentration of negatively charged nitrogen-vacancy defects ($NV^-$) equal to or greater than 100 ppb (parts-per-billion);

a concentration of point defects other than the $NV^-$ defects of below 200 ppm (parts-per-million);

a total nitrogen concentration equal to or greater than 10 ppm;

a concentration of all non-nitrogen point defects equal to or less than 1 ppm;

wherein at least one major face of the thin plate of synthetic single crystal diamond material comprises surface termination species which have zero nuclear spin and/or zero electron spin; and wherein the product of the concentration of $NV^-$ defects and decoherence time $T_2$ in the thin plate of synthetic single crystal diamond material is at least 0.1 ppm μs.

2. A thin plate of synthetic single crystal diamond material according to claim 1, wherein the thickness of the thin plate of synthetic single crystal diamond material is in a range: 500 nm to 30 μm, 1 μm to 20 μm, or 5 μm to 10 μm.

3. A thin plate of synthetic single crystal diamond material according to claim 1, wherein the concentration of $NV^-$ defects is equal to or greater than 1 ppm, 5 ppm, 10 ppm, or 30 ppm.

4. A thin plate of synthetic single crystal diamond material according to claim 1, wherein the concentration of $NV^-$ defects is equal to or less than 200 ppm, 150 ppm, 100 ppm, or 50 ppm.

5. A thin plate of synthetic single crystal diamond material according to claim 1, wherein an average projected planar distance between $NV^-$ defects is equal to or greater than 500 nm, 1 μm, 2 μm, 5 μm, 8 μm, 10 μm, 20 μm, or 50 μm.

6. A thin plate of synthetic single crystal diamond material according to claim 1, wherein the concentration of point defects other than the $NV^-$ defects is equal to or less than 150 ppm 100 ppm, 50 ppm, 20 ppm, 10 ppm, or 5 ppm.

7. A thin plate of synthetic single crystal diamond material according to claim 1, wherein a total nitrogen concentration is equal to or greater than 20 ppm, 50 ppm, 100 ppm, 150 ppm, 200 ppm, 250 ppm, 300 ppm, 400 ppm, or 600 ppm and wherein a concentration of all non-nitrogen point defects is equal to or less than 1/10, 1/100, or 1/1000 of these levels.

8. A thin plate of synthetic single crystal diamond material according to claim 1, wherein the thin plate of synthetic single crystal diamond material has one or more of the following characteristics:

(1) a birefringence in a direction perpendicular to the thin plate of synthetic single crystal diamond material equal to or less than $5\times10^{-5}$, $1\times10^{-5}$, $5\times10^{-6}$, or $1\times10^{-6}$;

(2) a density of extended defects as characterised by X-ray topography equal to or less than 400 per $cm^2$, 300 per $cm^2$, 200 per $cm^2$, or 100 per $cm^2$;

(3) a FWHM ("Full Width at Half Maximum") X-ray rocking curve width for a (004) reflection equal to or less than 50 arc seconds, 20 arc seconds, 10 arc seconds, 7 arc seconds, 5 arc seconds, 3 arc seconds, 2 arc seconds, or 1.5 arc seconds. wherein birefringence in a direction perpendicular to the thin plate of synthetic single crystal diamond material is equal to or less than $5\times10^{-5}$, $1\times10^{-5}$, $5\times10^{-6}$, or $1\times10^{-6}$.

9. A thin plate of synthetic single crystal diamond material according to claim 1, wherein the synthetic single crystal diamond material is synthetic HPHT single crystal diamond material.

10. A thin plate of synthetic single crystal diamond material according to claim 1, wherein both major faces of the thin plate of synthetic single crystal diamond material comprise surface termination species which have zero nuclear spin and/or zero electron spin.

11. A thin plate of synthetic single crystal diamond material according to claim 1, wherein the surface termination species have zero nuclear spin and zero electron spin.

12. A thin plate of synthetic single crystal diamond material according to claim 1, wherein the $NV^-$ defects have a decoherence time $T_2$ equal to or greater than 0.05 ms, 0.1 ms, 0.3 ms, 0.6 ms, 1 ms, 5 ms, or 15 ms, with corresponding $T_2^*$ values equal to or less than 400 μs, 200 μs, 150 μs, 100 μs, 75 μs, 50 μs, 20 μs, or 1 μs.

13. A thin plate of synthetic single crystal diamond material according to claim 1, wherein the product of the concentration of $NV^-$ defects and decoherence time $T_2$ is at least 1 ppm μs, 10 ppm μs, 20 ppm μs, 30 ppm μs, 50 ppm μs, 100 ppm μs, 200 ppm μs, 500 ppm μs, 1000 ppm μs, or 5000 ppm μs.

14. A thin plate of synthetic single crystal diamond material according to claim 1, wherein the thin plate of synthetic single crystal diamond material is formed wholly from the synthetic single crystal diamond material.

15. A device comprising:

a device component comprising a thin plate of synthetic single crystal diamond material according to claim 1; and a light source for optically pumping one or more of the $NV^-$ defects in the synthetic single crystal diamond material.

* * * * *